United States Patent [19]

Hrib et al.

[11] Patent Number: 5,041,445
[45] Date of Patent: Aug. 20, 1991

[54] 3-(1-THIAZOLIDINYLBUTYL-4-PIPERAZINYL)-TH-INDAZOLES

[75] Inventors: Nicholas J. Hrib, Somerville; Joseph T. Strupczewski, Flemington; John G. Jurcak, Somerset, all of N.J.; Kenneth Bordeau, Upper Black Eddy, Pa.

[73] Assignee: Hoechst-Roussel Pharmaceuticals Incorporated, Somerville, N.J.

[21] Appl. No.: 526,089

[22] Filed: May 21, 1990

[51] Int. Cl.$^5$ .................. A61K 31/495; C07D 417/14
[52] U.S. Cl. .................... 514/254; 544/230; 544/369
[58] Field of Search .............. 544/369, 230; 514/254

[56] References Cited

U.S. PATENT DOCUMENTS

| | | | |
|---|---|---|---|
| 4,100,282 | 7/1978 | Renth et al. | 544/392 |
| 4,448,777 | 5/1984 | Heinemann et al. | 548/372 |
| 4,775,761 | 10/1988 | Strupczewski | 544/297 |
| 4,933,453 | 6/1990 | Hrib et al. | 546/199 |

Primary Examiner—Cecilia Shen
Attorney, Agent, or Firm—Elliott Korsen

[57] ABSTRACT

This invention relates to 3-[1-thiazolidinylbutyl-4-piperazinyl]-1H-indazoles of the formula

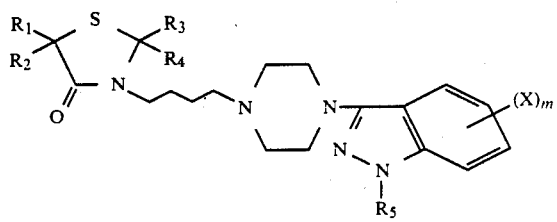

where $R_1$ and $R_2$ are each independently hydrogen or loweralkyl or $R_1$ and $R_2$ taken together with the carbon atom to which they are attached form a cyclopentane, cyclohexane or cycloheptane ring; $R_3$ and $R_4$ are independently hydrogen or loweralkyl or $R_3$ and $R_4$ taken together with the carbon atom to which they are attached form a cyclopentane, cyclohexane or cycloheptane ring; $R_5$ is hydrogen, loweralkyl, alkanoyl or aroyl; X is hydrogen, halogen, loweralkyl or alkoxy; m is an integer of 1 to 3, the pharmaceutically acceptable acid addition salts thereof and where applicable, the optical, geometrical and stereoisomers and racemic mixtures thereof. The compounds of this invention are useful as antipsychotic agents.

22 Claims, No Drawings

3-(1-THIAZOLIDINYLBUTYL-4-PIPERAZINYL)-1H-INDAZOLES

This invention relates to compounds of the formula

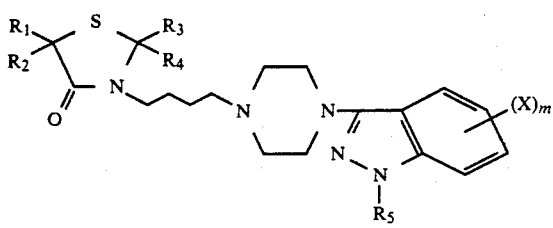

where $R_1$ and $R_2$ are each independently hydrogen or loweralkyl or $R_1$ and $R_2$ taken together with the carbon atom to which they are attached form a cyclopentane, cyclohexane or cycloheptane ring; $R_3$ and $R_4$ are independently hydrogen or loweralkyl or $R_3$ and $R_4$ taken together with the carbon atom to which they are attached form a cyclopentane, cyclohexane or cycloheptane ring; $R_5$ is hydrogen, loweralkyl, alkanoyl or aroyl; X is hydrogen, halogen, loweralkyl or alkoxy; m is an integer of 1 to 3, the pharmaceutically acceptable acid addition salts thereof and where applicable, the optical, geometrical and stereoisomers and racemic mixtures thereof. The compounds of this invention are useful as antipsychotic agents.

Preferred embodiments of the invention are those of Compound I where $R_1$ and $R_2$ taken together with the carbon atom to which they are attached form a cycloalkyl ring; X is fluorine and $R_5$ is hydrogen.

Throughout the specification and appended claims, a given chemical formula or name shall encompass all geometric, optical and stereoisomers thereof and racemic mixtures where such isomers and mixtures exist.

In the above definitions, the term "lower" means the group it is describing contains from 1 to 6 carbon atoms. The term "alkyl" refers to a straight or branched chain hydrocarbon containing no unsaturation, e.g., methyl, ethyl, isopropyl, t-butyl, neopentyl, n-hexyl, etc.; the term "alkoxy" refers to a monovalent substituent which consists of an alkyl group linked through an ether oxygen having its free valence bond from the ether oxygen, e.g., methoxy, ethoxy, propoxy, butoxy, pentoxy, etc.; the term alkanoyl refers to a substituent having the formula

alkyl-C—, where alkyl is as previously defined e.g., acetyl, etc.; the term aroyl refers to a substituent having the formula

aryl-C—, e.g. benzoyl, naphthoyl, etc., where aryl is a group of the formula

where Z is hydrogen, halogen, loweralkyl, loweralkoxy, trifluoromethyl, nitro and amino, and n is an integer of 1 to 3, e.g., phenyl, o-tolyl, m-methoxyphenyl, etc.; the term "halogen" refers to a member of the halogen family consisting of fluorine, chlorine, bromine and iodine.

The compounds of the present invention are prepared in the following manner:

Compound II of the formula

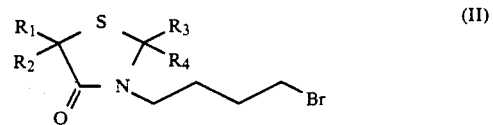

is reacted with Compound III of the formula

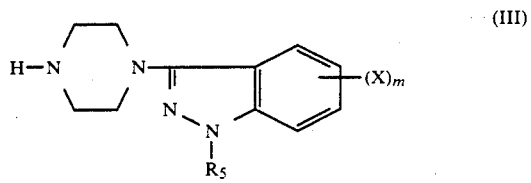

to afford Compound I of the invention of the formula

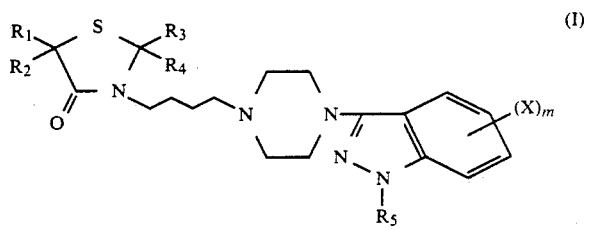

The above reaction is typically conducted in the presence of a suitable medium such as dimethylformamide or acetonitrile, an acid scavenger such as potassium carbonate or sodium carbonate and a catalytic amount of potassium iodide or sodium iodide at a temperature of about 25° to 120° C.

To prepare Compound I where $R_5$=loweralkyl, Compound I, where $R_5$ is hydrogen, is reacted with NaH or other suitable alkylating agent in a suitable medium such as dimethylformamide or acetonitrile at a temperature of 60° to 85° C.

Compound II is typically prepared as follows. A compound of the formula

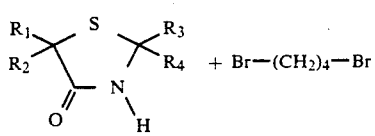

is reacted with 1,4-dibromobutane to afford Compound II. This reaction is typically conducted in the presence of a suitable medium such as dimethylformamide or tetrahydrofuran and a base such as potassium hydroxide, sodium hydroxide or sodium hydride at a temperature of about 23° to 70° C.

Compound III is prepared as disclosed in pending U.S. application Ser. No. 405,161, filed Sept. 11, 1989.

One can obtain Compound IV of the formula

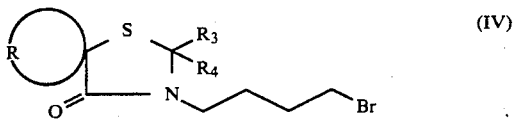

(IV)

where the divalent group—R—plus the spiro carbon as combined constitutes a cyclopentane, cyclohexane or cycloheptane ring, in the following manner.

3-(4-bromobutyl)-4-thiazolidinone of the formula

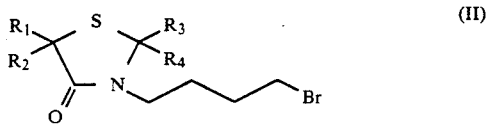

(II)

where $R_1$ and $R_2$ are hydrogen is reacted with lithium bis(trimethylsilyl)amide and Compound V of the formula Hal—$R_6$—Hal (V)

where $R_6$ is loweralkyl and Hal is Br or I, in a suitable medium such as tetrahydrofuran and at a low temperature such as $-75°$ to $-50°$ C., to afford compound IV.

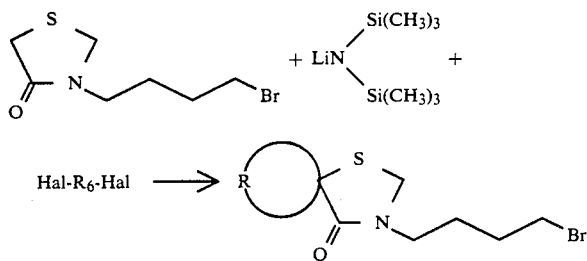

Similarly, if one uses a monobromide or monoiodide of the formula $R_6$—Hal in place of Compound V, one can obtain compound VI and/or Compound VII.

If one desires to obtain Compound VI of the formula

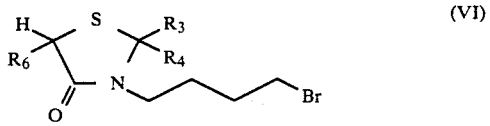

(VI)

as the predominant product, it is preferable to adjust the molar ratio between $R_6$—Hal, Compound IIa of the formula

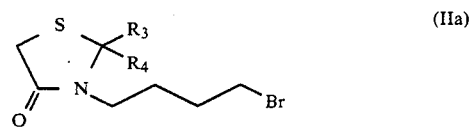

(IIa)

and lithium bis(trimethylsilyl)amide to about 1:1; whereas if one desires to obtain compound VII of the formula

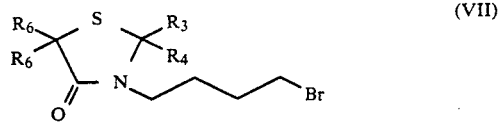

(VII)

as the predominant product, it is preferable to adjust the molar ratio to about 1:2.

The compounds of the present invention are potentially useful as antipsychotic agents as determined in the Climbing Mouse Assay (CMA).

The Climbing Mouse Assay is described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. The apomorphine is injected subcutaneously at 1.5 mg/kg, a dose causing climbing in all subjects for 30 minutes. Compounds to be tested for antipsychotic activity are injected intraperitoneally (i.p.) 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice with: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless, over longer periods of time. By contrast, climbs due to mere motion stimulation usually last only a few seconds.

The climbing scores are individually totaled (maximum score: 6 per mouse over 3 readings) and the total score of the control group (vehicle intraperitoneally; apomorphine subcutaneously) is set to 100%. $ED_{50}$ values with 95% confidence limits, calculated by linear regression analyses of some of the compounds of this invention are presented in Table 1.

TABLE 1

| Compound | Climbing Mice Assay $ED_{50}$, Mg/kg |
|---|---|
| 3-(4-(1-[1H-Indazol-3-yl]-4-piperizinyl)-butyl)-5,5-dimethyl-4-thiazolidine | 1.3 i.p. |
| 3-(4-(1-[1H-Indazol-3-yl]-4-piperazinyl)-butyl)-1-thia-3-azaspiro[4.4]nonan-4-one | 1.3 i.p. |
|  | 2.7 p.o. |
| 3-(4-(1-[1H-Indazol-3-yl]-4-piperazinyl)-butyl)-1-thia-3-azaspiro[4.5]decan-4-one | 0.65 i.p. |
| 3-(4-[1-(6-Fluoro-1H-indazol-3-yl)-4-piperazinyl]butyl)-5-methyl-4-thazolidinone | 0.11 i.p. |
| 3-(4-[1-(6-Fluoro-1H-indzol-3-yl)-4-piperazinyl]butyl)-1-thia-3-azaspiro[4.5]decan-4-one | 0.04 i.p. |
|  | 0.67 p.o. |
| Clozapine (standard) | 8.1 i.p. |

TABLE 1-continued

| Compound | Climbing Mice Assay ED$_{50}$, Mg/kg |
|---|---|
| Sulpiride (standard) | 14.5 i.p. |

Antipsychotic response is achieved when the compounds of this invention are administered to a subject requiring such treatment at an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not to any extent, limit the scope of the invention.

Effective amounts of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0-300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ®, corn starch and the like; a lubricant such as magnesium stearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
3-(4-(1-[6-fluoro-1H-indazol-3-yl]-4-piperazinyl)butyl)-2,5,5-trimethyl-4-thiazolidinone;
3-(4-(1-[6-fluoro-1H-indazol-3-yl]-4-piperazinyl)butyl)-2,2,5,5-tetramethyl-4-thiazolidinone;
3-(4-(1-[6-fluoro-1H-indazol-3-yl]-4-piperazinyl)butyl)-2-methyl-1-thia-3-azaspiro[4.4]nonan-4-one;
3-(4-(1H-indazol-3-yl)-4-piperazinyl)butyl)-2-methyl-1-thia-3-azaspiro[4.5]decan-4-one;
3-(4-(1-[6-fluoro-1H-indazol-3-yl]-4-piperazinyl)butyl)-2-methyl-1-thia-3-azaspiro[4.5]decan-4-one;
3-(4-(1-[6-fluoro-1H-indazol-3-yl]-4-piperazinyl)butyl)-2,2-dimethyl-1-thia-3-azaspiro[4.5]decan-4-one;
3-(4-[1-acetyl-1H-indazol-3-yl]-4-piperazinyl)butyl)-5-methyl-4-thiazolidinone;
3-(4-[1-(1-acetyl-6-fluoro-1H-indazol-3-yl)-4-piperazinyl]butyl)-1-thia-3-azaspiro[4.5]decan-4-one;
3-(4-(1-[1-acetyl-6-fluoro-1H-indazol-3-yl]-4-piperazinyl)butyl)-5-methyl-4-thiazolidinone;
3-(4-(1-[1-benzoyl-6-fluoro-1H-indazol-3-yl]-4-piperazinyl)butyl)-5-methyl-4-thiazolidinone;
3-(4-(1-[1-benzoyl-6-fluoro-1H-indazol-3-yl]-4-piperazinyl)butyl)-1-thia-3-azaspiro[4.5]decan-4-one.

The following examples are for illustrative purposes only and are not to be construed as limiting the invention. All temperatures are given in degrees centigrade (°C.).

EXAMPLE 1 a. 3-(4-bromobutyl)-4-thiazolidinone

A mixture of 4-oxothiazolidine (25 g,) dimethylformamide (500 ml), and KOH (27.16 g) was stirred under $N_2$ at room temperature for 1.5 hours. To the resulting mixture was added 1,4-dibromobutane (101 ml) and stirring was continued at room temperature for 44 hours. The reaction mixture was poured into $H_2O$ (1000 ml) and the aqueous mixture was extracted three times with 300 ml portions of ethyl acetate. The combined extracts were washed with H₂O (300 ml) and brine (300 ml), dried over Na₂SO₄, and concentrated in vacuo to an oil. HPLC of a 44.95 g aliquot yielded 7.15 g of an oil which upon distillation yielded a clear liquid, b.p. 134°–137° C/0.12 mmHg.

Analysis: Calculated for $C_7H_{12}BrNOS$: 35.30% C; 5.08% H; 5.88% N. Found: 35.24% C; 5.09% H; 5.83% N.

b. 3-(4-Bromobutyl)-5-methyl-4-thiazolidinone

To a −74° C. solution of 3-(4-bromobutyl)-4-thiazolidinone (5.20 g) and tetrahydrofuran (70 ml) under nitrogen was rapidly added lithium bis(trimethylsilyl)amide (0.023 mol) in tetrahydrofuran (23 ml) followed immediately by methyl iodide (7.74 g). The resulting solution was stirred for 20 min (cooled by the CO₂/isopropanol bath), allowed to warm to −40° C., and acidified with 1N HCl (200 ml). The resulting aqueous mixture was extracted three times with 100 ml portions of 25% benzene/ether. The combined extracts were washed with brine (200 ml), dried (Na₂SO₄), and concentrated in vacuo to a liquid which was chromatographed on silica gel, eluting with 45% ethyl acetate in hexanes, yielding 3.84 g of an oil. The oil was distilled to give 2.60 g of 3-(4-bromobutyl)-5-methyl-4-thiazolidinone, b.p. 123°–125° C. at 0.20 mm Hg.

Analysis: Calculated for $C_8H_{14}BrNOS$: 38.10% C; 5.60% H; 5.55% N. Found: 38.12% C; 5.58% H; 5.48% N.

EXAMPLE 2 a. 3-(4-bromobutyl)-2,5,5-trimethyl-4-thiazolidinone

To a −73° C. solution of 3-(4-bromobutyl)-2-methyl-4-thiazolidinone (6.00 g), methyl iodide (10.99 g), and tetrahydrofuran (50 ml) under nitrogen was added lithium bis(trimethylsilyl)amide (0.0500 mol) in tetrahydrofuran (50 ml) at a rate to maintain the internal temperature at less than −55° C. The resulting solution was stirred at less than −55° C. for 10 min, allowed to warm to −40° C. at which temperature 1N HCl (250 ml) was added. The aqueous mixture was extracted three times with 125 ml portions of 25% benzene/ether. The combined extracts were washed with brine (200 ml), dried (Na₂SO₄), and concentrated to a liquid which was chromatographed on silica gel (345 g), eluting with a 35–65% gradient of ethyl acetate in hexanes, yielding 5.07 g of a liquid. The liquid was distilled to give 3.80 g of 3-(4-bromobutyl)-2,5,5-trimethyl-4-thiazolidinone, b.p. 109°–114° C. at 0.20 mmHg.

Analysis: Calculated for $C_{10}H_{18}BrNOS$: 42.86% C; 6.47% H; 5.00% N. Found: 42.93% C; 6.47% H; 5.00% N.

b. 3-[4-[1-(1H-indazol-3-yl)piperazinyl]-2,5,5-trimethyl-4-thiazolidinone

A mixture of 3-(4-bromobutyl)-2,5,5-trimethyl-4-thiazolidinone (4.00 g), 1-(1H-indazol-3-yl)piperazine (3.18 g), K₂CO₃ (6.00 g), NaI (300 g), and acetonitrile (200 ml) was heated at 75° C. under nitrogen. After 17 hours, TLC analysis showed the absence of starting bromide. The mixture was cooled to ambient temperature, filtered, the inorganics washed with dichloromethane, and the filtrate concentrated under reduced pressure to a liquid. The crude residue was taken up in dichloromethane (220 ml), washed with H₂O (130 ml), brine (130 ml), dried (NaSO₄), and concentrated to a liquid. The liquid was purified by chromatography on silica gel. Elution with 5% methanol in dichloromethane afforded 4.22 g of a solid. Recrystallization from ether/hexanes provided 2.22 g of 3-[4-[1-(1H-indazol-3-yl)piperazinyl]butyl]-2,5,5-trimethyl-4-thiazolidinone, m.p. 111°–112° C.

Analysis: Calculated for $C_{21}H_{31}N_5OS$: 62.81% C; 7.78% H; 17.44% N. Found: 62.88% C; 7.66% H; 17.47% N.

EXAMPLE 3 a. 3-(4-bromobutyl)-1-thia-3-azaspiro[4.5]decan-4-one

To a solution of 3-(4-bromobutyl)-4-thiazolidinone (25 g) in tetrahydrofuran (350 ml) cooled to −60° C., was added 1,5-diiodopentane (100 g). The resulting slurry was allowed to cool to −65° C. and a solution of lithium bis(trimethylsilyl)amide in hexanes (220 ml) was added dropwise over a period of 30 minutes while maintaining the internal temperature at or below −55° C. The resulting mixture was stirred for 15 minutes and the internal temperature allowed to rise to 0° C. 0.5N HCl (500 ml) was added to quench the reaction and the mixture was concentrated in vacuo to remove the THF. The aqueous mixture was extracted twice with 250 ml portions of ether, washed with water (400 ml) and brine (400 ml), dried (Na₂SO₄) and concentrated to a liquid. The liquid was chromatographed on silica gel (elution with 20% ethyl acetate/hexane) to give a liquid.

b. 3-(4-(1-[1H-indazol-3-yl]-4-piperazinyl)butyl)-1-thia-3-azaspiro[4.5]decan-4-one A mixture of 3-(4-bromobutyl)-1-thia-3-azaspiro[4.5]decan-4-one (4.06 g), 3-(1-piperazinyl)-1H-indazole (2.95 g), K₂CO₃ (5.50 g), and acetonitrile (250 ml) was heated at 80° C. under nitrogen. After 20 hours, TLC analysis (silica gel, 50% ether/hexanes) showed only a trace of starting bromide. The mixture was cooled to ambient temperature, ethyl acetate (150 ml) added, the inorganics filtered, and the filtrate concentrated under reduced pressure. The residue was taken up in dichloromethane (220 ml), washed with H₂O (110 ml), brine (130 ml), dried (NaSO₄), and concentrated to a foam. The foam was chromatographed on silica gel, eluting with 10% methanol in dichloromethane, to give 4.83 g of a foam which solidified upon addition of ethyl acetate. The solid was recrystallized from ethyl acetate/hexanes yielding 2.76 g of 3-(4-(1-[1H-indazol-3-yl]-4-piperazinyl)butyl)-1-thia-3-azaspiro[4.5]decan-4-one, m.p. 159°–161° C.

Analysis: Calculated for $C_{23}H_{33}N_5OS$: 64.60% C; 7.78% H; 16.38% N. Found: 64.50% C; 7.86% H; 16.49% N.

EXAMPLE 4

2-(4-(4-(1-[1H-Indazol-3-yl]piperazinyl))-butyl)-5-methyl-thiazolidinone

A mixture of 3-(4-bromobutyl)-5-methyl-4-thiazolidinone (3.9 g), 3-(1-piperazinyl)-1H-indazole (3.0 g), K₂CO₃ (4.1 g) and NaI (200 mg) in 150 ml dry acetontrile was heated to 80° C. with stirring under N₂. After 18 hours no starting piperazine remained as judged by TLC. The mixture was cooled to room temperature and filtered and the filtrate concentrated in vacuo. The residue was chromatographed on silica using 5:95 methanol:ethyl acetate eluent to give a solid. This product was recrystallized from ether/hexane to provide 2.593 g of 2-(4-(4-(1-[1H-indazol-3-yl]-piperazinyl))butyl)-5-methyl-thiazolidinone, m.p. 105°–108° C.

Analysis: Calculated for $C_{19}H_{27}N_5OS$: 61.10% C; 7.29% H; 18.75% N. Found: 61.13% C; 7.21% H; 18.67% N.

EXAMPLE 5 a. 3-(4-bromobutyl)-1-thia-3-azaspiro[4.4]nonan-4-one

To a −76° C. solution of 3-(4-bromobutyl)-4-thiazolidinone (4.75 g) and tetrahydorfuran (120 ml) under nitrogen was added lithium bis(trimethylsilyl)amide (0.0203 mol) in tetrahydrofuran (20.3 ml) rapidly, immediately followed by 1,4-diiodobutane (15.51 g). After 12 min, a solution of lithium bis (trimethylsilylamide (0.0620 mol) in tetrahydrofuran (62 ml) was added over a period of 30 minutes. The resulting reaction was allowed to warm to −45° C. at which temperature 1N HCl (250 ml) was added. The resulting aqueous mixture was extracted 4 times with 110 ml portions of ether. The combined extracts were washed with brine (250 ml), dried ($Na_2SO_4$), and concentrated to a liquid. The liquid was chromatographed on silica gel (elution with 40% ethyl acetate in hexanes) to give 3.34 g of a liquid. The liquid was distilled using a short path distillation apparatus at 0.20 mmHg to give 2.35 g of 3-(4-bromobutyl)-1-thia-3-azaspiro[4.4]nonan-4-one.

Analysis: Calculated for $C_{11}H_{18}NOS$: 45.21% C; 6.21% H; 4.79% N. Found: 45.33% C; 6.19% H; 4.81% N.

b. 3-(4-(1-[1H-Indazol-3-yl]-4-piperazinyl)butyl)-1thia-3-azaspiro[4.4]nonan-4-one A mixture of 3-(4-bromobutyl)-1-thia-3-azaspiro[4.4]nonan-4-one (4.00 g), 3-(1-piperazinyl)-1H-indazole (3.05 g), $K_2CO_3$ (6.63 g), NaI (320 mg), and acetonitrile (210 ml) was heated at 85° C. under nitrogen. After 4 hours, TLC analysis (silica gel, 40% ethyl acetate in hexanes) showed the starting bromide to be consumed. The mixture was cooled to ambient temperature, ethyl acetate (100 ml) was added, the inorganics filtered, and the filtrate concentrated under reduced pressure. The residue was taken up in dichloromethane (210 ml), washed with $H_2O$ (100 ml), brine (100 ml), dried ($Na_2SO_4$), and concentrated under reduced pressure to a liquid. The liquid was purified by chromatography on silica gel, eluting with 5% methanol in dichloromethane, to give 4.75 g of a foam which solidified upon addition of ether. The solid was recrystallized from ethyl acetate to yield 3.51 g of 3-(4-(1-[1H-Indazol-3-yl]-4-piperazinyl)butyl)-1-thia-3-azaspiro[4.4]nonan-4-one, m.p. 166.5°–168° C.

Analysis: Calculated for $C_{22}H_{31}N_5OS$: 63.89% C; 7.56% H; 16.93% N. Found: 63.61% C; 7.61% H; 16.73% N.

EXAMPLE 6

3-(4-(1-[1H-Indazol-3-yl]-4-piperazinyl)butyl-2-methyl-1-thia-3-azaspiro[4.4]nonan-4-one A mixture of 3-(4-bromobutyl)-2-methyl-1-thia-3-azaspiro[4.4]nonan-4-one (4.20 g), 3-(1-piperazinyl)-1H-indazole (3.0 g), $K_2CO_3$ (5.68 g), NaI (310 mg), and acetonitrile (220 ml) was heated between 60° and 80° C. under nitrogen. After 18 hours, TLC analysis showed only a trace of the starting bromide. The mixture was cooled to ambient temperature, ethyl acetate (150 ml) was added, the inorganics filtered, and the filtrate concentrated under reduced pressure. The residue was taken up in dichloromethane (230 ml), washed with $H_2O$ (130 ml), brine (130 ml), dried ($Na_2SO_4$), and concentrated to a foam. The foam was chromatographed on silica gel, diluting with 8% methanol in dichloromethane, to furnish 5.04 g of a foam which solidified upon addition of ether/hexanes. The solid was recrystallized from ethyl acetate/hexanes to give 3.72 g of 3-(4-(1-[1H-indazol-3-yl]-4-piperazinyl)butyl)-2-methyl-1-thia-3-azaspiro[4.4]non-4-one, m.p. 113°–115° C.

Analysis: Calculated for $C_{23}H_{33}N_5OS$: 64.60% C; 7.78% H; 16.38% N. Found: 64.71% C; 8.08% H; 16.52% N.

EXAMPLE 7 a. 6-Fluoro-3-(1-piperazinyl)-1H-indazole hydrochloride

To a stirred mixture under $N_2$ of 4-(6-fluoro-1-phenylsulfonyl-1H-indazol-3-yl)-1-piperazinecarbonitrile (25.4 g) in tetrahydrofuran (400 ml), was added, dropwise, lithium aluminum hydride in tetrahydrofuran (130 ml of a 1M solution). The reaction was stirred and refluxed for 3 hours, cooled in an ice bath and $H_2O$ was added dropwise. The reaction was filtered and the filter cake was washed with tetrahydrofuran and twice with methanol. Concentration of the filtrate afforded a gum, which when triturated with ether afforded 14.6 g of a solid. The solid was dissolved in methanol and ethereal HCl was added to the solution until it was acidic. Ether was then added to the solution, which initially precipitated a gum. The supernatant solution was decanted from the gum, and upon addition of more ether to the solution, 5.4 g of a hydrochloride salt was collected. Trituration of the gum with refluxing ethyl acetate gave an addition 3.2 g of salt. The larger sample was recrystallized twice from methanol/ether to afford 2.2 g of 6-fluoro-3-(1-piperazinyl)-1H-indazole hydrochloride, m.p. 268°–270° C.

Analysis: Calculated for $C_{11}H_{13}FN_4 \cdot HCl$: 51.47% C; 5.50% H; 21.82% N. Found: 51.38% C; 5.37% H; 21.61% N.

b. 3-{4-[1-(6-Fluoro-1H-indazol-3-yl)-4-piperazinyl]-butyl}-1-thia-3-azaspiro[4.5]decan-4-one A mixture of 6-fluoro-3-(1-piperazinyl)-1H-indazole hydrochloride (4.0 g), potassium carbonate (6.5 g), 3-(4-bromobutyl)-1-thia-3-azaspiro[4.5]decan-4-one (5.2 g), potassium iodide (200 mg) and dimethylformamide (100 ml) was stirred at 75° C. under $N_2$ for 17 hours. The cooled reaction was poured into $H_2O$ and the aqueous mixture was extracted with ethyl acetate. The ethyl acetate extract was washed with $H_2O$, dried with $MgSO_4$ and concentrated to yield 10.3 g of a solid. The sample was purified by preparative high performance liquid chromatography (HPLC) (silica gel, 6% methanol-dichloromethane as eluent) to provide 4.1 g. Recrystallization of the compound from isopropyl alcohol afforded 3.1 g of 3-{4-[1-(6-fluoro-1H-indazol-3-yl)-4-piperazinyl]butyl}-1-thia-3-azaspiro[4.5]decan-4-one, m.p. 163°–165° C.

Analysis: Calculated for $C_{23}H_{32}FN_5OS$: 62.00% C; 7.24% H; 15.72% N. Found: 61.81% C; 7.15% H; 15.62% N.

EXAMPLE 8

3-{4-[1-(6-Fluoro-1H-indazol-3-yl)-4-piperazinyl]-butyl}-1-thia-3-azaspiro[4.4]nonan-4-one A mixture of 6-fluoro-3-(1-piperazinyl)-1H-indazole hydrochloride (4.0 g), potassium carbonate (6.5 g), 3-(4-bromobutyl)-1-thia-3-azaspiro[4.4]nonan-4-one (5.0 g), dimethylformamide (100 ml) and potassium iodide (200 mg) was stirred for 16 hours at 65° under $N_2$. The cooled reaction was then poured into $H_2O$ and the aqueous mixture was extracted with ethyl acetate. The ethyl acetate extract was dried with $MgSO_4$ and concentrated to yield 6.8 g of a solid. The sample was purified by preparative HPLC (silica gel, 6% methanol-dichloromethane) to afford 3.0 g. Recrystallization from isopropyl alcohol provided 2.1 g of 3-{4-[1-(6-fluoro-1H-indazol-3-yl)-4-piperazinyl]-butyl}-1-thia-3-azaspiro[4.4]nonan-4-one, m.p. 132°–134°.

Analysis: Calculated for $C_{22}H_{30}FN_5OS$: 61.23% C; 7.01% H; 16.23% N. Found: 61.37% C; 6.93% H; 16.21% N.

EXAMPLE 9

3-{4-[1-(6-Fluoro-1H-indazol-3-yl)-piperazinyl]butyl}-5-methyl-4-thiazolidinone

A mixture of 6-fluoro-3-(1-piperazinyl)-1H-indazole hydrochloride (4.0 g), potassium carbonate (6.5 g), 3-(4-bromobutyl)-5-methyl-4-thiazolidinone (4.3 g), potassium iodide (200 mg) and dimethylformamide (100 ml) was stirred at 80° under $N_2$ for 7.5 hours and then let stand for 16 hours at room temperature. The reaction mixture was poured into $H_2O$ and the aqueous mixture was extracted with ethyl acetate. The ethyl acetate extract was dried with $MgSO_4$ and concentrated to yield 8.0 g of a liquid. The sample was purified by preparative HPLC (silica gel, 6% methanol-dichloromethane) to afford 3.6 g. Recrystallization from isopropyl alcohol provided 2.2 g of 3-{4-[1-(6-fluoro-1H-indazol-3-yl)-piperazinyl]butyl}-5-methyl-4-thiazolidinone, m.p. 119°–120°.

Analysis: Calculated for $C_{19}H_{26}FN_5OS$: 58.29% C; 6.69% H; 17.89% N. Found: 58.24% C; 6.74% H; 17.80% N.

EXAMPLE 10

3-(4-(1-[6-Fluoro-1H-indazol-3-yl]-4-piperazinyl)-butyl)-5,5-dimethyl-4-thiazolidinone To a stirred mixture of 6-fluoro-3-(1-piperazinyl)-1H-indazole (4.4 g), $K_2CO_3$ (2.8 g), 3-(4-bromobutyl)-5,5-dimethyl-4-thiazolidinone (6.6 g) and dimethylformamide (75 ml) was heated at 75° for 4 hours. The reaction was poured into $H_2O$, and the aqueous mixture extracted with ethyl acetate. The ethyl acetate was washed ($H_2O$), dried ($MgSO_4$) and the solvent concentrated to afford an oil. Upon standing the oil crystallized, and when the mass was triturated with ether, 3.3 g of a solid was collected. The compound was recrystallized from toluene-hexane to yield 2.8 g of 3-(4-(1-[6-fluoro-1H-indazol-3-yl]-4-piperazinyl)-butyl)-5,5-dimethyl-4-thiazolidinone, m.p. 123°–125° C.

Analysis: Calculated for $C_{20}H_{28}FN_5OS$: 59.24% C; 6.96% H; 17.27% N. Found: 59.37% C; 6.99% H; 17.32% N.

EXAMPLE 11 a. 3-(1-piperazinyl)-1H-indazole

A mixture of 4-(1H-indazol-3-yl)-1-piperazinecarbonitrile (8.0 g), and 25% $H_2SO_4$ (100 ml) was stirred at reflux for 4.5 hours. The reaction was cooled in an ice bath and made basic by the dropwise addition of 50% NaOH. The basic solution was extracted with ethyl acetate. The ethyl acetate was washed with $H_2O$, dried with $MgSO_4$ and concentrated to afford 5.2 g of the desired compound, as a solid. The sample was recrystallized twice from toluene to afford 3.0 g of the unsubstituted indazole, m.p. 153°–155° C.

Analysis: Calculated for $C_{11}H_{14}N_4$: 65.32% C; 6.98% H; 27.70% N. Found: 65.21% C; 6.99% H; 27.80% N.

b. 3-(4-(1-[1H-Indazol-3-yl]-4-piperazinyl)-butyl)-5,5-dimethyl-4-thiazolidinone A stirred mixture of 3-(1-piperazinyl)-1H-indazole (5.0 g), 3-(4-bromobutyl)-5,5-dimethyl-4-thiazolidinone (6.6 g) and dimethylformamide (120 ml) was heated at 70°–75° for 1.25 hours. The reaction was poured into $H_2O$, dried ($MgSO_4$) and the solvent concentrated to afford a solid. The solid was triturated with hexane and was collected to yield 7.2 g of a solid. Recrystallization from toluene afforded 5.7 g of 3-(4-(1-[1H-indazol-3-yl]-4-piperazinyl)-butyl)-5,5-dimethyl-4-thiazolidinone, m.p. 139°–142° C.

Analysis: Calculated for $C_{20}H_{29}N_5OS$: 61.98% C; 7.54% H; 18.07% N. Found: 62.12% C; 7.51% H; 17.85% N.

EXAMPLE 12

3-{4-[1-(1-Methyl-1H-indazol-3-yl)-4-piperazinyl]-butyl}-5,5-dimethyl-4-thiazolidine To a stirred mixture of sodium hydride (0.66 g), in dimethylformamide (20 ml) under $N_2$ was added, 3-{4-[1-(1H-indazol-3-yl)-4-piperazinyl]-butyl}-5,5-dimethyl-4-thiazolidine (4.4 g) dissolved in hot dimethylformamide (30 ml). The mixture was allowed to stir at ambient temperature for one hour and was then chilled to −1° C. in an ice-salt bath. Iodomethane (1.78 g) dissolved in dimethylformamide (10 ml) was added dropwise so that the temperature did not exceed 1° C. After complete addition the ice bath was removed and the reaction was allowed to stir under $N_2$ at ambient temperature for 3.5 hours. The reaction was poured into $H_2O$, dried with $MgSO_4$ and concentrated to afford 5.0 g of a liquid. The liquid was triturated with hexane to produce a solid, which was collected and dried to afford 2.5 g. The compound was recrystallized from hexane yielding 2.0 g 3-{4-[1-(1-methyl-1H-indazol-3-yl)-4-piperazinyl]butyl}-5,5-dimethyl-4-thiazolidine, m.p. 91°–93° C.

Analysis: Calculated for $C_{21}H_{31}N_5OS$: 62.81% C; 7.78% H; 17.44% N. Found: 62.97% C; 7.80% H; 17.42% N.

We claim:

1. A compound of the formula

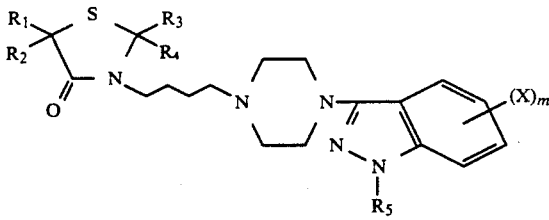

where $R_1$ and $R_2$ are each independently hydrogen or loweralkyl or $R_1$ and $R_2$ taken together with the carbon atom to which they are attached form a cyclopentane, cyclohexane or cycloheptane ring; $R_3$ and $R_4$ are independently hydrogen or loweralkyl or $R_3$ and $R_4$ taken together with the carbon atom to which they are attached form a cyclopentane, cyclohexane or cycloheptane ring; $R_5$ is hydrogen, loweralkyl, alkanoyl or aroyl; X is hydrogen, halogen, loweralkyl or alkoxy; m is an integer of 1 to 3; or a pharmaceutically acceptable acid addition salt thereof and where applicable, the optical, geometrical and stereoisomers and racemic mixtures thereof.

2. The compound according to claim 1 wherein $R_1$ and $R_2$ are loweralkyl.

3. The compound according to claim 2 wherein $R_3$ is loweralkyl.

4. The compound according to claim 2 wherein $R_5$ is loweralkyl.

5. The compound according to claim 2 wherein X is selected from hydrogen or halogen.

6. The compound according to claim 1 wherein $R_1$ and $R_2$ taken together with the carbon atom to which they are attached form a cyclopentane, cyclohexane or cycloheptane ring.

7. The compound according to claim 6 where $R_3$ is loweralkyl.

8. The compound according to claim 6 wherein X is selected from hydrogen and halogen.

9. The compound according to claim 1 wherein $R_1$ is loweralkyl and $R_2$ is hydrogen.

10. The compound according to claim 2 which is 3-(4-(1-[1H-indazol-3-yl]-4-piperazinyl)-butyl)-5,5-dimethyl-4-thiazolidinone.

11. The compound according to claim 3 which is 3-(4-(1-(1H-indazol-3-yl)-4-piperazinyl)butyl)-2,5,5-trimethyl-4-thiazolidinone.

12. The compound according to claim 4 which is 3-{4-[1-(1-methyl-1H-indazol-3-yl)-4-piperazinyl]-butyl}-5,5-dimethyl-4-thiazolidine.

13. The compound according to claim 5 which is 3-(4-(1-[6-fluoro-1H-indazol-3-yl]-4-piperazinyl)butyl)-5,5-dimethyl-4-thiazolidinone.

14. The compound according to claim 7 which is 3-(4-(1-[1H-indazol-3-yl]-4-piperazinyl)butyl-2-methyl-1-thia-3-azaspiro[4.4]nonan-4-one.

15. The compound according to claim 8 which is 3-(4-[1-(6-fluoro-1H-indazol-3-yl)-4-piperazinyl]butyl)-1-thia-3-azaspiro[4.4]nonan-4-one.

16. The compound according to claim 8 which is 3-(4-[1-(6-fluoro-1H-indazol-3-yl)-4-piperazinyl]butyl)-1-thia-3-azaspiro[4.5]decan-4-one.

17. The compound according to claim 6 which is 3-(4-(1-[1H-indazol-3-yl]-4-piperazinyl)butyl)-1-thia-3-azaspiro[4.4]nonan-4-one.

18. The compound according to claim 6 which is 3-(4-(1-[1H-indazol-3-yl]-4piperazinyl)butyl)-1-thia-3-azaspiro[4.5]decan-4-one.

19. The compound according to claim 9 which is 3-(4-[1-(6-fluoro-1H-indazol-3-yl)-4-piperazinyl]butyl)-5-methyl-4-thiazolidinone.

20. The compound according to claim 9 which is 3-(4-(1-(1H-indazol-3-yl)-4-piperazinyl)butyl)-5-methyl-4-thiazolidinone.

21. An antipsychotic composition comprising an effective psychosis alleviating amount of a compound as defined in claim 1 and a suitable carrier therefor.

22. A method of treating a patient in need of relief from psychosis which comprises administration of an effective psychosis alleviating amount of a compound is defined in claim 1.

* * * * *

UNITED STATES PATENT AND TRADEMARK OFFICE
CERTIFICATE OF CORRECTION

PATENT NO. : 5,041,445

DATED : August 20, 1991

INVENTOR(S) : NICHOLAS J. HRIB, JOSEPH T. STRUPCZEWSKI, JOHN G. JURCAK AND KENNETH BORDEAU

It is certified that error appears in the above-identified patent and that said Letters Patent is hereby corrected as shown below:

On the title page, Item (54):

Please delete the title and replace with

"3-(1-THIAZOLIDINYLBUTYL-4-PIPERAZINYL)-1H-INDAZOLES"

Signed and Sealed this

First Day of June, 1993

Attest:

MICHAEL K. KIRK

Attesting Officer     Acting Commissioner of Patents and Trademarks